United States Patent [19]
Parmley

[11] Patent Number: 4,464,113
[45] Date of Patent: Aug. 7, 1984

[54] SURGICAL DRILL APPARATUS

[76] Inventor: Richard J. Parmley, 4272 Flora Pl., St. Louis, Mo. 63110

[21] Appl. No.: 387,247

[22] Filed: Jun. 10, 1982

[51] Int. Cl.³ .................. A61G 1/14; A61G 15/00
[52] U.S. Cl. .................................... 433/77; 433/101
[58] Field of Search .............. 433/101, 103, 77, 78, 433/79, 119

[56] References Cited
U.S. PATENT DOCUMENTS 3,081,542  3/1963  Sherfey ........................... 433/101
4,286,949  9/1981  Holt ................................ 433/101

Primary Examiner—Robert Peshock

[57] ABSTRACT

Surgical drill apparatus includes a stand with a base and an upright column, a sterilizable water tank manually mountable on and demountable from the column, a gas flow control valve, equipped with a pedal, mounted on the base, oxygen lines connected to the valve, hence to the tank, thence to a surgical drill, and a water line connected to the water tank and the surgical drill. An oxygen line connected to one side of the valve at one end is connected to the hospital oxygen supply at its other end. The oxygen and water lines are plastic and equipped with quick-disconnect fittings complementary to fittings on the water tank. The water tank is of a size to hold sufficient water to permit the completion of any operation in which the drill is likely to be used. A simple, repeatedly sterilizable or disposable pinch valve is used to control the flow of water to the drill.

15 Claims, 14 Drawing Figures

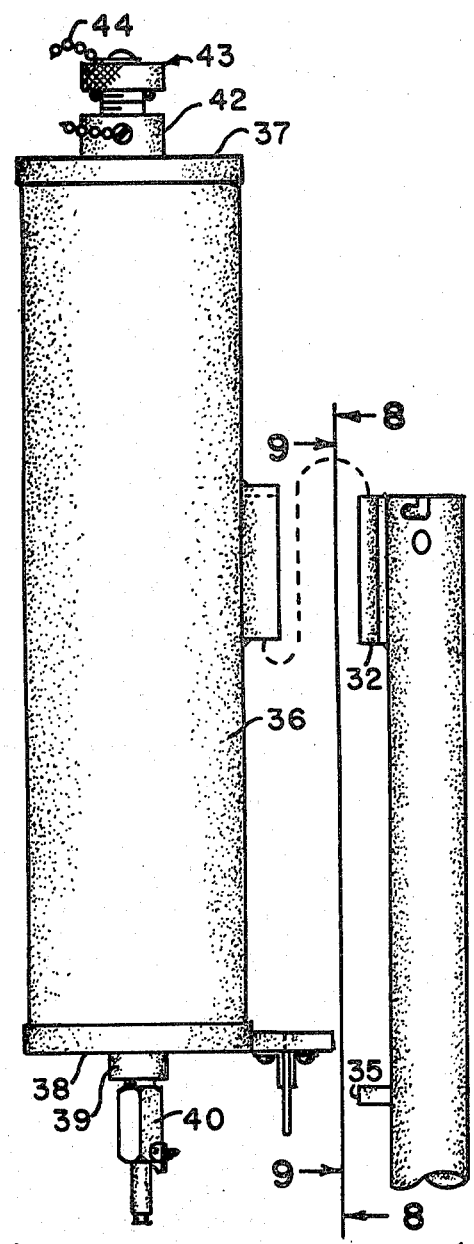
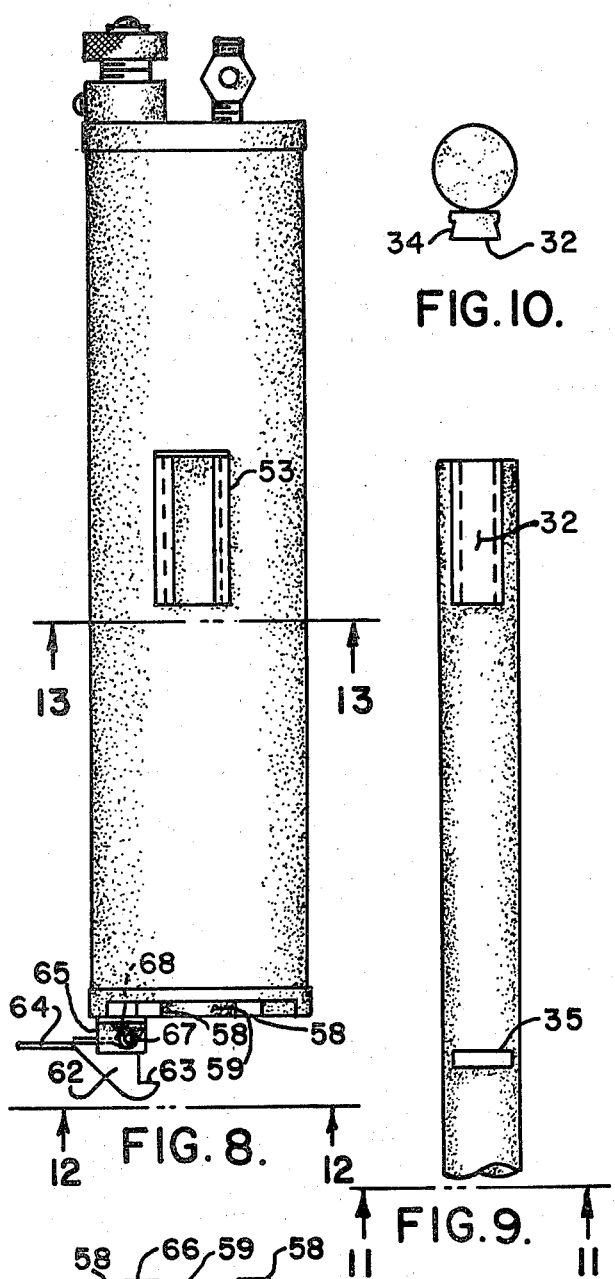
FIG. 10.
FIG. 8.
FIG. 9.
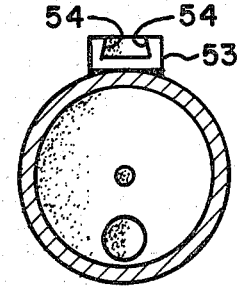
FIG. 7.
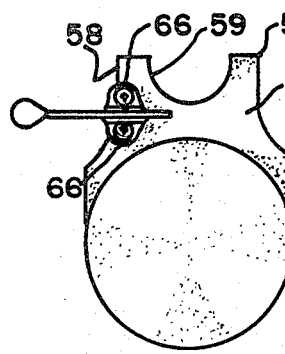
FIG. 11.
FIG. 13.
FIG. 12.

SURGICAL DRILL APPARATUS

BACKGROUND OF THE INVENTION

Hospitals are increasingly required to have dental staffs, who commonly operate in the hospital operating rooms. This invention has particular application to hospital dental surgery, but it also has application to any surgery in which a rotary surgical tool such as a handpiece mounted drill or burr or small saw is used. The terms "drill" and "dental drill" are used hereinafter to encompass any such surgical tool, complete with handpiece or other mounting device to which gas and liquid connections are made. Hospitals have been ill-equipped to accommodate the dental staffs in respect of dental drill operating equipment. Often, dental surgeons have brought their own equipment. It is undesirable to use electrically operated tools in the operating room because of the danger of sparks. One approach to hospital-supplied equipment that was tried was a portable drill operated by compressed air. In this equipment, made during the early 1960's by Star Dental Manufacturing Company of Philadelphia, Pa., most of the tubing connections were permanent, and when the reserve water tank was autoclaved, which had to be done frequently because the tank was small, the attached tubing tended to rupture. The use of compressed air necessitated the provision of a separate ceramic air filter, and if compressed air tanks were used, they were not sterile. A needle valve was used to control the flow of water, but certain carbon steel components rusted. The manufacture of the equipment evidently ceased after about five years.

The present invention provides solutions to the problems that led to the abandonment of that apparatus.

One of the objects of this invention is to provide portable surgical drill apparatus suitable for use in hospitals that is simple in construction and operation, easily sterilized, easily used, rugged, long-lasting, and safe, as compared with apparatus known heretofore.

Other objects will become apparent to those skilled in the art in the light of the following description and accompanying drawing.

SUMMARY OF THE INVENTION

In accordance with this invention, generally stated, surgical drill apparatus is provided that includes a support, a sterilizable water tank manually mountable on and demountable from the support, an oxygen line fitting on the tank, an oxygen line connected to the fitting and to a rotary drill, and a foot operated oxygen flow controlling valve connected to an oxygen line and to a source of oxygen under pressure. The support preferably takes the form of a base at least 12" square with a heavy platform section, sloping to thin outer edges along each side, and an upright, all of stainless steel. A control valve, equipped with a broad, easily located foot pedal, is mounted on the base. In the preferred embodiment, the water tank has a capacity of 1200 cc, and 1000 cc of water are introduced, leaving a head space of 200 cc. The water tank is equipped with a T-fitting with a through passage in its head communicating with a passage in a stem mounted in the top wall of the tank, and a water tube fitting in its bottom wall. All of the fittings on the tank are equipped with stainless steel quick-disconnects, with suitable keepers. The tank is also provided with an internally threaded filler boss into which a filler closure, with an externally threaded stem, a knurled head and an O-ring in the arris between them, is threadedly mounted. The closure is mounted on the tank by means of a chain, so that it can not fall or be misplaced when it is unmounted. Because the various oxygen and water lines are equipped with quick disconnect fittings complementary to the fittings on the tank, the lines can be made of plastic, and gas sterilized, while the tank is ordinarily autoclaved. Because the water line is made of resilient plastic, the flow of water from the tank is regulated by a simple pinch valve, which may be a standard intravenous (IV) drip control.

BRIEF DESCRIPTION OF THE DRAWINGS

In the drawing,

FIG. 7 is an enlarged view in side elevation, partly in section, of the water tank with oxygen fittings removed and the upright, with cap removed, partly broken away and partly in section;

FIG. 8 is a view in rear elevation taken along the line 8—8 of FIG. 7;

FIG. 9 is a view in front elevation taken along the line 9—9 of FIG. 7;

FIG. 10 is a top plan view of the upright shown in FIG. 7;

FIG. 11 is a plan view taken along the line 11—11 of FIG. 9;

FIG. 12 is a plan view taken along the line 12—12 of FIG. 8;

FIG. 13 is a sectional view taken along the line 13—13 of FIG. 8; and

DESCRIPTION OF THE PREFERRED EMBODIMENT

Figure 1:
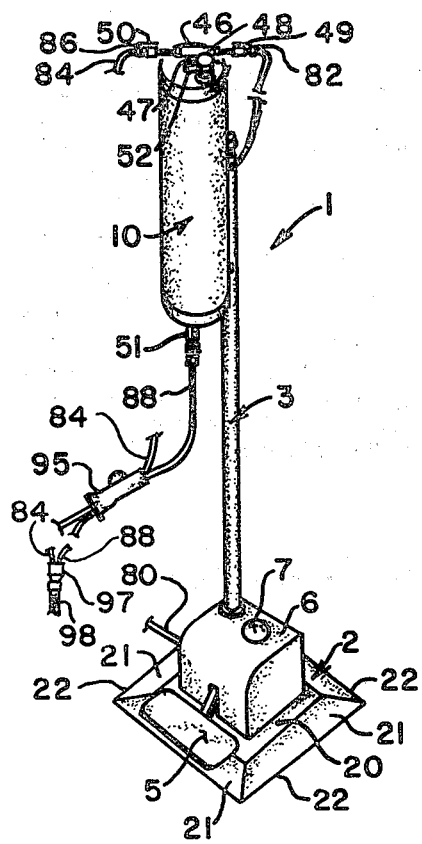
FIG. 1 is a view in perspective of one embodiment of drill apparatus of this invention, with tubing broken away.
Figure 14:
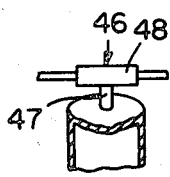
FIG. 14 is a fragmentary view in side elevation of the top of the water tank.
Figure 2:
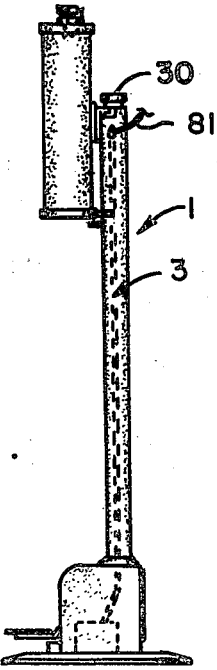
FIG. 2 is a view in side elevation.
Figure 3:
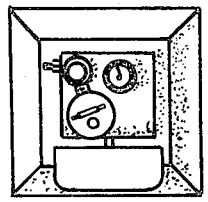
FIG. 3 is a top plan view.
Figure 4:
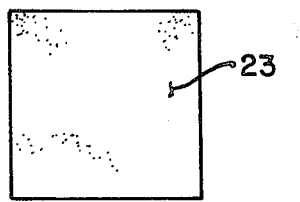
FIG. 4 is a bottom plan view.
Figure 5:
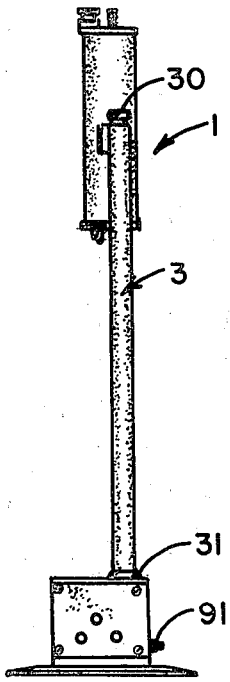
FIG. 5 is a view in rear elevation.
Figure 6:
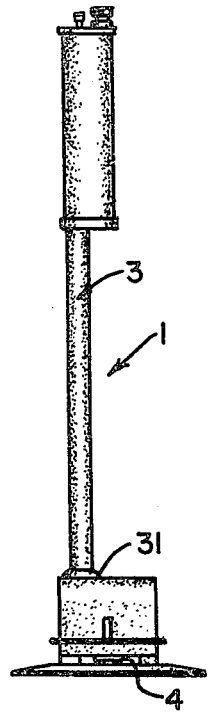
FIG. 6 is a view in front elevation.

Referring now to the drawing for one illustrative embodiment of apparatus of this invention, reference numeral 1 represents the assembled apparatus, which includes a base 2, an upright or column 3, a valve 4 shown somewhat formally in FIG. 6, a valve pedal 5, connected to the valve and extending through an opening in a valve housing 6, a pressure gage 7 and a water tank 10.

The base 2 has a heavy, flat-topped central platform 20 and sloped side panels 21 integral with the central platform, with thin outer edges 22. In this embodiment the base has a flat bottom surface 23.

The column 3 has a cap 30 which, in this embodiment, is shown as being removably mounted with a bayonet joint in the hollow column. At its lower end, the column is welded or screwed or otherwise securely anchored to the base. It projects through the upper wall of the housing 6, and is provided with a seal ring or grommet 31. At its lower end, the column 3 has an opening to receive a valve to tank tube 81. Near its upper end, the column has an opening for the tube 81, and, at right angles to the opening, an elongated guide and mounting block 32 extending axially of the column and welded or otherwise secured to the outside of the column, as best shown in FIGS. 7, 9 and 10. The long sides of the block 32 are channeled vertically, to provide ribs 34 that are chamfered convergently toward the column, as shown particularly in FIG. 10. Vertically below the block 32, a latch plate-stop 35 is secured to the column.

The water tank 10 has a cylindrical side wall 36, a top wall 37 and a bottom wall 38. In its bottom wall 38, an outwardly projecting annular fitting boss 39, internally threaded, provides an opening communicating with the interior of the tank. A quick-disconnect fitting 40, with the usual keeper, is threadedly mounted in the fitting boss 39, as shown particularly in FIG. 7. On its top wall, the tank has two bosses, an internally threaded annular oxygen fitting boss 52 and an internally threaded annular filling boss 42, both of which also provide openings that communicate with the interior of the tank. The filler opening is closed when the device is in use by a knurled-headed closure 43 with a threaded stem and an O-ring seated in the arris between the stem and the head, as shown in FIG. 7. The closure 43 is connected to the boss 42 by means of a chain 44 fastened at one end by a stud or rivet to the boss 42, and at its other, by a swivel on a headed pin in the top of the closure.

A T-fitting 46 has an externally threaded stem 47 mounted in the oxygen fitting boss 52 to communicate with the inside of the tank, and a head 48 through which a passage, communicating at its center with a passage in the stem 47, extends. At one end of the head, an oxygen supply female quick-disconnect fitting 49, with its keeper, is mounted, and in the other end of the head, an oxygen outflow female quick-disconnect fitting 50, with its keeper, is mounted.

A channel-shaped bracket 53 is secured to the outside of the side wall 36 about midway of the height of the tank. The bracket 53 has parallel wings 54 extending axially and shaped and proportioned to embrace the ribs 34 of the block 32. A filler-yoke plate 56, with arms 58 defining a seat 59 shaped complementarily to a segment of the column 3, is secured to the bottom wall 38 of the tank, the center of the seat 59 being in vertical alignment with the center of the channel defined by the wings 54. A latch 61 is mounted on the underside of the yoke plate 56 as shown particularly in FIGS. 7, 8 and 12. The latch 61 in this embodiment includes a latch plate 62 with a nose 63 serving as a keeper, and a handle 64, a knuckle 65 with ears through which mounting studs 66 pass into the plate 56, a pintle 67 by which the latch plate 62 is hingedly mounted to the knuckle, and a leaf spring 68 mounted to bias the latch plate toward the latch plate stop 35. The nose 63 is positioned to extend under the plate stop 35 when the water tank is mounted on the column to prevent accidental upward movement of the tank with respect to the column.

The complete apparatus includes an oxygen supply tube 80, one end of which is attached to a fitting 91 communicating with the valve 4 at one end, and, by way of a male quick-connect fitting on the line, with a source of oxygen under pressure, not here shown, at the other; the plastic valve-to-tank tube 81 equipped at its upper end with a male quick-disconnect fitting 82 to be coupled with the female fitting 49 of the T-fitting 46; a plastic tank-to-drill tube 84 equipped with a male quick-disconnect fitting 86 coupled with the female fitting 50 of the T-fitting 46 at one end, and connected at its other end by a standard fitting 97 to a drill 98, and a plastic water tube 88 with a female quick-disconnect coupled with the male quick-disconnect 40 at one end and connected at its other, by means of the fitting 97, to the drill. Intermediate the ends of the water tube 88, a pinch valve 95, which, in the preferred embodiment, is a standard IV drip control, is mounted, preferably near the handpiece.

The base is preferably made of stainless steel, at least 12" square and preferably 14" square, at least ⅜" thick through the area of the platform 20 and tapering outwardly along the panels to a thickness of ⅛" at the edges 22. The valve housing 6 is also preferably of stainless steel, as is the column 3. The valve pedal 5, by means of which the surgeon can control the volume of oxygen supplied to the drill, hence the speed of the drill, is preferably at least 5" wide and extends from the housing sufficently far to make the pedal easy to locate and depress. The column 3 is, in this embodiment, made of 1" stainless steel tubing, with a wall thickness sufficient to preclude any bending in use. It is high enough to bring the tank above the level of the operating table. The water tank 10 is also made of stainless steel as are the closure 43 and its chain and swivel, its fittings, and the block 53 and plate 56. The tank preferably has a capacity of about 1200 cc, of which 1000 cc is occupied by sterile water at the beginning of the use of the apparatus. The two sections of tubing connected to the oxygen fitting of the tank and the one piece connected to the water tube can be packaged in plastic sterilizing bags and gas sterilized.

The apparatus of this invention can be utilized as follows. The surgeons and scrub nurses, after a pre-surgical scrub, are gowned and gloved and are then considered to be in a sterile state. The surgical drape packet is opened, the circulating nurse removes the outer covers of the surgical drill unit and hands them to the scrub nurse who opens the inner containers. The patient is prepped and draped in the usual way.

The circulating nurse connects the hospital oxygen supply line from the valve 4 to the hospital oxygen supply, and positions the base and upright adjacent the patient. The surgeon connects the water tube and the two oxygen tubes to the water tank and attaches the handpiece to the water tube and the tank-to-drill tube. Utilizing a sterile funnel, the circulating nurse pours into the water tank 1000 cc of sterile water. The surgeon then puts the knurled filler closure in the opening and tightens it with finger pressure. The tank is then mounted on the upright. The circulating nurse then attaches the valve-to-tank oxygen supply tube to the tank fitting and the unit is now ready for operation. Any adjustments to the water flow are made with the plastic IV drip control.

With this procedure, there is complete freedom from introducing any bacterial or viral contamination to the patient.

The hospital oxygen supply is almost universally carried by piping from a central source, so that no tanks have to be wheeled into the operating room. The oxygen is sterile and prefiltered, so that no additional filter is necessary. The water tank and its closure and fittings are made of stainless steel, except for the O-ring on the closure, and can be autoclaved for an indefinite number of times. The various pieces of tubing and their fittings can be gas sterilized repeatedly, extending the life of the tubing at least tenfold over the length of life of tubing that was autoclaved with the water tank. The provision of a broad base with tapered side panels and the large foot pedal substantially precludes accidental tipping and makes the operation of the valve, hence the drill, easy.

Numerous variations in the construction of apparatus of this invention, within the scope of the appended claims, will occur to those skilled in the art in the light of the foregoing disclosure. By way of example, the base can be made round or polygonal in plan. The quick-disconnect fittings can be reversed with the male fittings on the tank oxygen T-fitting and female fittings on the tubes, for example. A different pinch valve can be substituted for the IV drip control, although the latter has the advantages of being relatively inexpensive, readily available and familiar to doctors and nurses. Other liquids besides or in addition to water, can be used as the cooling and flushing liquid, and the term "water" as applied to the tank, is intended to encompass any suitable liquid. Because hospitals are likely to supply oxygen under a known, well regulated pressure, the gauge 7 may be omitted in some cases. Different forms of caps or closures may be used. In the illustrative embodiment described, the quick connect or disconnect fittings on the oxygen to drill tube and the water tube have been stainless steel, and, as indicated, the tubes can be gas sterilized. However, it is entirely feasible to make these fittings, as well as the drill fitting, of plastic, preferably moulded onto the tubes, with the pinch valve premounted, and to dispose of the tubes after use. Hospitals may find this to be the preferred embodiment, because of the economies of labor, and the economies of hospital management and billing involved. These are merely illustrative.

I claim:

1. In an operating room in which dental surgery is performed on a patient on an operating table, portable surgical drill apparatus comprising a support including a stable base and an elongated, substantially vertical member, a sterilizable water tank, manually mountable on and demountable from said vertical member near the upper end thereof, the upper end of said tank when the tank is mounted on the support being substantially as high as the operating table, an oxygen fitting on said tank communicating with the interior of said tank, an oxygen line connected to said fitting to pressurize water in said tank, a rotary turbine drill connected to said oxygen line, a water tube communicating from the tank to the drill and a manipulable oxygen flow-controlling valve connected to said oxygen line and to a source of said oxygen under pressure.

2. The apparatus of claim 1 wherein said oxygen fitting has two oxygen line fittings, one to connect a valve-to-tank tube to the tank and the other to connect a tank-to-drill tube to the tank, both communicating with the interior of the tank, both said fittings being stainless steel quick-disconnects.

3. The apparatus of claim 1 including a filling opening boss in the top of said water tank and a water fitting boss in the bottom thereof, a quick-disconnect fitting mounted in said water fitting boss and a flexible, diametrically resiliently deformable water line connected to said fitting to communicate with the interior of said tank.

4. The apparatus of claim 3 including a pressure-tight closure for mounting in and demounting from said filling opening boss and means for retaining said closure on said tank when said closure is demounted from said filling opening boss.

5. The apparatus of claim 3 including a pinch valve mounted on said water tube for selectively resiliently deforming said water tube to control flow of water through said tube.

6. The apparatus of claim 5 wherein the pinch valve is a plastic IV drip control.

7. The apparatus of claim 1 wherein the support comprises a stainless steel base on the order of 14" square, with a thickness at its thickest dimension of at least ⅜" and being tapered outboardly to a thickness of about ⅛" at its outer edges, and a stainless steel upright column.

8. The apparatus of claim 7 including an elongated guide block secured to said column and a latch plate-stop secured to said column between said guide block and said base, a guide block-embracing channel secured to said tank for slidable mounting of said tank on and demounting from said guide block, and a selectively releasable latch secured to said tank for engaging said latch plate.

9. The apparatus of claim 8 wherein the latch is mounted on a filler-yoke plate projecting from said tank and partly embracing said column.

10. The apparatus of claim 8 wherein said foot pedal connected to said valve projects above an outwardly downwardly tapered marginal portion of said base, said foot pedal being on the order of at least 5" wide.

11. The apparatus of claim 1 including a tank to drill oxygen tube and a tank to drill water tube, wherein the tubes are made of plastic, and fittings on said tubes complementary to quick disconnect fittings on said oxygen fitting, are moulded onto the tubes.

12. The apparatus of claim 11 wherein the tubes have moulded onto their other ends a drill fitting.

13. The apparatus of claim 12 wherein the tank to drill water tube has a pinch valve premounted between the moulded fittings.

14. The apparatus of claim 1 wherein the base rests flat on the floor of the operating room, and the manipulable valve is a foot operated valve positioned in said oxygen line between said source and said tank and drill, with a pedal having a free edge adjacent a margin of the base, hingedly mounted on said base inboard of the outer edge of said base for movement up and down.

15. The apparatus of claim 1 wherein the oxygen fitting on said tank is a T fitting, the stem of which is mounted in the top of said tank and the cross bar of which is connected at one end to a valve-to-tank tube portion of the oxygen line and at the other end, to a tank-to-drill tube.

\* \* \* \* \*